(12) United States Patent
Wilson et al.

(10) Patent No.: US 7,577,286 B2
(45) Date of Patent: Aug. 18, 2009

(54) MACHINE VISION EQUIPMENT

(75) Inventors: Ronald F. Wilson, Page Hill (GB); Gary J. Pitt, Newport Pagnell (GB); Timothy G. Irons, Kempston (GB); William A. H. Everitt, Commercial Road (GB)

(73) Assignee: Molins PLC, Milton Keynes (GB)

( * ) Notice: Subject to any disclaimer, the term of this patent is extended or adjusted under 35 U.S.C. 154(b) by 411 days.

(21) Appl. No.: 10/549,787

(22) PCT Filed: Mar. 19, 2004

(86) PCT No.: PCT/GB2004/001177

§ 371 (c)(1),
(2), (4) Date: Aug. 3, 2006

(87) PCT Pub. No.: WO2004/082409

PCT Pub. Date: Sep. 30, 2004

(65) Prior Publication Data

US 2007/0031023 A1  Feb. 8, 2007

(30) Foreign Application Priority Data

Mar. 20, 2003  (GB)  ................................. 0306467.2

(51) Int. Cl.
*G06K 9/00* (2006.01)
(52) U.S. Cl. .................. 382/141; 382/291; 382/294; 348/94; 356/139.06
(58) Field of Classification Search .................. 382/294, 382/291, 154, 141, 151, 287, 204; 29/833, 29/720; 356/139.06, 604, 512, 614; 396/91; 901/47; 700/259; 701/300; 348/94, E5.037, 348/86, E5.042; 250/237 G, 206.1; 209/939; 352/53; 318/640; 345/419
See application file for complete search history.

(56) References Cited

U.S. PATENT DOCUMENTS 5,768,401 A * 6/1998 Csipkes et al. ............... 382/255
6,169,600 B1 * 1/2001 Ludlow .................... 356/237.1

FOREIGN PATENT DOCUMENTS

| EP | 0 758 742 A2 | 2/1997 |
| EP | 1 028 305 A2 | 8/2000 |
| EP | 1028305 | * 8/2000 |
| FR | 2 256 394 | 7/1975 |

* cited by examiner

*Primary Examiner*—Sheela C Chawan
(74) *Attorney, Agent, or Firm*—Woodard, Emhardt, Moriarty, McNett & Henry LLP

(57) ABSTRACT

A method of setting-up machine vision equipment is disclosed. The equipment includes a camera defining a field of view, processing means for determining physical properties of a test object, and first supporting means for supporting a test object at a predetermined distance from the camera within the field of view. The method is characterised by providing second supporting means for supporting a reference object, placing a reference object having at least one known dimension on the second supporting means, moving one or more of the cameras, the first supporting means and the second supporting means to bring the reference object within the field of view at the predetermined distance from the camera, imaging the reference object to obtain an image, and processing the image to determine the optimum configuration of the imaging means, and adjusting the imaging means configuration to the optimum configuration.

24 Claims, 3 Drawing Sheets

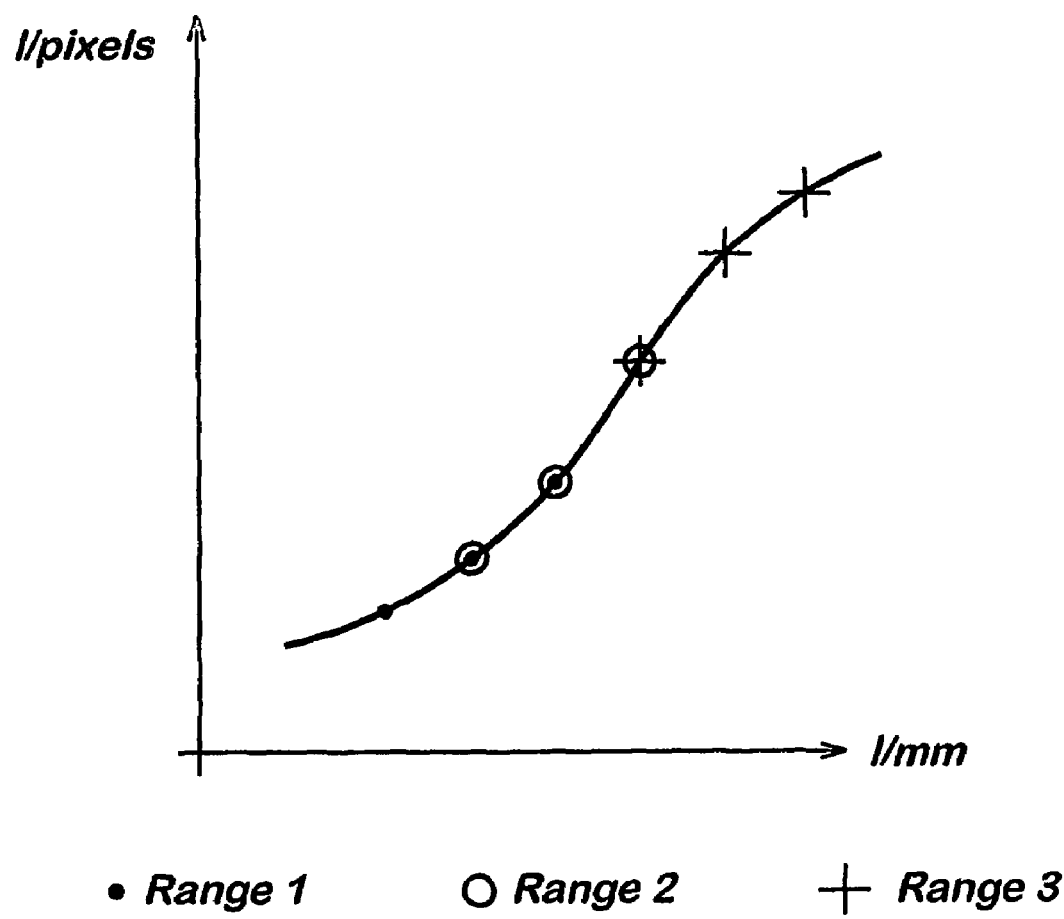

MACHINE VISION EQUIPMENT

CROSS-REFERENCES TO RELATED APPLICATIONS

This application is a National Stage of International Application PCT/GB2004/001177, filed Mar. 19, 2004. Applicant claims foreign priority benefits under 35 U.S.C. 119(a)-(d) of the following foreign application for patent: United Kingdom Application No. 0306467.2, filed Mar. 20, 2003, which is hereby incorporated by reference in its entirety.

BACKGROUND OF THE INVENTION

The present invention provides improvements in or relating to machine vision equipment, and has particular reference to a method and apparatus for automatically setting-up such machine vision equipment.

Co-pending international patent application no. PCT/GB2004/001181, corresponding to earlier United Kingdom application no. 0306468.0, the contents of which international application are fully incorporated herein by reference, discloses a method and apparatus for determining one or more physical properties of a rolled smoking article or filter rod, comprising positioning a rolled smoking article or filter rod within a field of view, illuminating the field of view, imaging the rolled smoking article or filter rod within the field of view to form an image, and analysing the image to determine one or more physical properties of the rolled smoking article or filter rod. Typically, the image is a digital image which is acquired using a digital camera, preferably a digital video camera. The image may be acquired using any wavelength or range of wavelengths, for example infrared light. Thus, the image comprises a digital array of pixels which may be analysed using suitable processing means to determine one or physical properties of the rolled smoking article or filter rod such as its length, diameter, ovality, and the like.

As described in co-pending PCT/GB2004/001181, analysis of the digital image may be performed using well-known algorithms to detect edges within the image.

Such algorithms may employ contrast levels for defining a point at which an edge is defined as being present, the length (in pixels) along a detected edge being used to determine a contiguous and true edge, and algorithms for carrying out statistical probability calculations to confirm that a detected edge is a true edge. A preferred technique for detecting an edge within an image comprises generating horizontal and vertical region projections within a region of interest of the image, and then analysing the projections in order to detect any significant edges. Such image processing techniques are not described further herein, but are described in a number of standard reference works including Sonka, et al., 1999, *Image Processing, Analysis and Machine Vision*, 2nd Edition, page 356 (6.35), Pacific Grove: PWS Publishing, ISBN 0-534-95393-X, the contents of which are incorporated herein by reference.

The accurate detection of edges within a digital image by imaging processing techniques of the kind described above relies on such edges being sharply in focus within the image, to allow the edges to be detected without undue exposure of the image which might lead to undesirable affects such as "blooming", which is associated with many digital imaging devices, particularly those comprising CCD-type sensors.

The machine vision equipment is also required to be calibrated to provide accurate conversion of distances measured in pixels in the image to actual distances measured, for example, in millimeters or inches.

Calibration of machine vision equipment is typically carried out using reference objects of accurately known dimensions. A known reference object comprises a machined solid steel cylinder having an accurately known diameter. Steel reference objects are used in view of their good dimensional stability. However, metal reference objects are not suitable for calibrating machine vision equipment of the kind described by co-pending PCT/GB2004/001181 in view of the high reflectance of the metal.

Furthermore, it is generally inconvenient manually to place a reference object in the field of view of the machine vision equipment for intermittent calibration and re-calibration.

There is therefore a need for a dimensionally stable reference object which is suitable for use for calibrating machine vision equipment of the kind disclosed by co-pending PCT/GB2004/001181.

There is also a requirement for a method of automatically setting-up such machine vision equipment.

In accordance with one aspect of the invention therefore there is provided a dimensionally stable reference object having at least one accurately known dimension which is fabricated from a ceramic material having a low reflectance or albedo value. Preferably, the reference object comprises a cylindrical bar having an accurately known diameter.

Said ceramic material may comprise a ceramic alumina. Preferably, the ceramic material has an alumina content of more than about 70% by weight, and more preferably more than about 90% or 95% by weight. The ceramic material should be substantially impervious and should have good refractory properties, for example, refractoriness up to about 1700° C. Apart from alumina, the ceramic material may comprise various other ceramic constituents, particularly magnesium oxide. In some embodiments, the ceramic material comprise about 99.7% weight alumina, with the balance being substantially magnesium oxide. A suitable ceramic material available commercially from W Haldenwanger Technishe Keramik GmbH & Co KG, Germany, under the trade mark "Alsint 99,7".

In another aspect of the present invention there is provided machine vision equipment incorporating automatic set-up means; said equipment comprising:

imaging means comprising a camera defining a field of view and being adapted to form an image of test object within said field of view, and processing means for processing said image for determining one or more physical properties of said test object; and first supporting means for supporting a test object within said field of view at a predetermined distance from said camera;

characterised by:

second supporting means for supporting a reference object having a least one accurately known dimension;

moving means for selectively moving one or more of the camera, the first supporting means, and the second supporting means such that a reference object placed on the second supporting means is disposed within the camera's field of view at said predetermined distance from said camera;

adjusting means for automatically adjusting the configuration of the imaging means;

optimum configuration determining means for determining the optimum configuration of said imaging means by processing one or more images of a reference object placed on a the second supporting means; and controlling means for controlling operation of the moving means, imaging means, adjusting means and optimum configuration determining means for bringing a reference object supported by said second supporting means into the camera's field of view, imaging said reference object, determining the optimum configuration of the imaging means, and adjusting the imaging means to said optimum configuration.

In yet another aspect of the present invention there is provided a method of setting-up machine vision equipment, said equipment comprising imaging means comprising a camera defining a field of view and being adapted to form an image of a test object within said field of view, and processing means for processing said image for determining one or more physical properties of said test object, and first supporting means for supporting a test object at a predetermined distance from the camera within the field of view;

said method being characterised by:

providing second supporting means for supporting at least one reference object;

placing a reference object having at least one accurately known dimension on said second supporting means;

selectively moving one or more of the camera, the first supporting means and the second supporting means, such that said reference object is brought into the camera's field of view at said predetermined distance from the camera;

imaging the reference object to obtain at least one image, and processing said at least one image to determine the optimum configuration of the imaging means;

and thereafter adjusting the configuration of the imaging means to said optimum configuration.

In accordance with the present invention therefore, a reference object having at least one accurately known dimension may be placed on the second supporting means, and when the machine vision equipment is required to be set-up, or the set-up of machine vision equipment is required to be checked, the controlling means cause the reference object on the second supporting means to be brought into the camera's field of view at the same predetermined distance from the camera as a test object on the first supporting means during normal operation of the machine vision equipment. The reference object is then imaged, and the image is processed to determine the optimum set-up of the imaging means; the imaging means are then adjusted to said optimum set-up. The reference object may then be removed from the camera's field of view and replaced by said first supporting means for use or continued use of the machine vision equipment for determining one or more physical properties of a test object.

In some embodiments, said optimum configuration determining means may be adapted for determining the optimum configuration of the imaging means by processing a plurality of images of said reference object obtained with said imaging means in different respective configurations, and said controlling means may be adapted to control said imaging means, adjusting means and optimum configuration determining means to obtain and process serial images of said reference object whilst adjusting progressively the configuration of the imaging means, and to determine the optimum configuration on the basis of said serial images.

Thus, as disclosed in co-pending PCT/GB2004/001181, the camera may comprise means for automatically adjusting the focal length of the camera. For example, the camera may comprise a barrel portion housing a lens, and said barrel portion may be provided with a gear which is adapted to be driven by a toothed belt from a DC motor controlled by said controlling means. As described above, it is important, when measuring dimensions of a test object by analysing a digital image of the test object to detect the presence of significant edges, to ensure that the image of the test object is properly in focus. Thus, in accordance with the present invention, the optimum configuration determining means may comprise optimum focal length determining means, and said controlling means may be adapted for controlling the adjusting means, imaging means and optimum focal length determining means to obtain and process serial images of the reference object at different respective focal lengths, and to determine the optimum focal length at which the reference object is best in focus, and for controlling the adjusting means thereafter to adjust the focal length of the camera to said optimum focal length.

The second supporting means are preferably configured to support a reference object having substantially the same shape and size in substantially the same orientation in the field of view as the test object. Where the test object comprises a rolled smoking article or filter rod, the reference object suitably comprises a cylindrical bar having substantially the same diameter as the rolled smoking article or filter rod. In order to measure the diameter of a rolled smoking article or filter rod, a digital image of the rolled smoking article or filter rod is analysed to detect opposite, substantially parallel edges of a profile of the rolled smoking article or filter rod in the image, which profile corresponds to a cross-section through the rolled smoking article or filter rod through its central axis. Thus, in order to ensure that said opposite edges are properly focused in the image, the camera should be focused on the centre axis of the rolled smoking article or filter rod. Preferably, therefore the second supporting means are configured to support a cylindrical reference bar in an orientation substantially orthogonal to the optical axis of the camera.

Preferably the camera comprises a digital camera which is adapted to form the image as a regular array of pixels.

In some embodiments, said configuration determining means may comprise calibration determining means adapted to compare an actual measured value of said at least one dimension of said reference object with said accurately known value; said adjusting means may be adapted for adjusting the calibration of said imaging means; said controlling means may be configured for controlling said imaging means, calibration determining means, and adjusting means, for measuring said at least one dimension of said reference object to obtain a measured value, comparing said measured value with the accurately known value, and adjusting the calibration of the imaging means accordingly, such that the measured value equals the known value. In this way, the controlling means may generate a calibrated conversion factor for converting distances in the image of a test object, measured in pixels, to actual distances, measured in, for example, millimeters or inches.

Those skilled in the art will know that diameter measurements using machine vision equipment may be sensitive to optical effects associated with the camera. Accordingly, a calibration curve of actual length versus pixels may be non-linear. Accordingly, it is desirable to calibrate the machine vision equipment at least two different known diameters, and then to interpolate between those known diameters to establish a calibrated scale.

Thus, in accordance with a particular aspect of the present invention said second supporting means may be adapted to support a plurality of reference objects, each having substantially the same shape as the test object, but each having a different respective, accurately known value of said at least one dimension; said moving means may be adapted for selectively moving said one or more of the camera, first supporting means and second supporting means to bring each reference object in turn into the camera's field of view at the predetermined distance from the camera; said calibration determining means may be adapted for comparing the measured value of said at least one dimension of each reference object with the respectively accurately known value, and to generate a calibration curve for said imaging means on the basis of said comparisons.

In some embodiments, said second supporting means may be adapted to support three reference objects. As described above, each reference object may comprise a cylindrical bar of accurately known diameter.

The reference objects may be interchangeable in order to calibrate the machine vision system for dimension measurements within different ranges. By supporting three reference objects the second supporting means may be adapted, for any given measurement range, to support reference objects having accurately known dimensions respectively at or towards each end of the measurement range and at an arbitrary dimension intermediate said two ends, for example substantially towards the middle of the measurement range.

Thus, the provision of five reference objects allows the machine vision equipment in accordance with the present invention to be calibrated with three-point calibration for use in three different, but overlapping, measurement ranges.

Conveniently, said second supporting means may comprise at least one holder for holding each reference object, each holder defining a v-shaped cavity which is configured to receive transversely the cylindrical reference bar at the same depth into the cavity regardless of the diameter of the bar. In some embodiments, said second supporting means may comprise two holders for holding each reference object, one holder at or towards each end of the respective bar. In this way, each reference object can easily be positioned at said predetermined distance from the camera, irrespective of the diameter of the reference object. It will be appreciated that by placing each reference object on the second supporting means at the same predetermined distance from the camera, the central axes of the reference objects will be positioned at different respective distances from the camera. However, the actual differences in diameter between the reference objects will be small, and within the allowed tolerance of the focus of the camera. Accordingly, there is no need in practice to re-adjust the focal length of the camera for imaging and calibrating against each reference object.

The present invention therefore provides improvements in or relating to machine vision equipment, particularly equipment of the kind described by co-pending PCT/GB2004/001181 by providing a method and apparatus for automatically setting-up the machine vision equipment; in particular to set-up automatically the focal length and calibration of the machine vision equipment. The present invention also provides a suitable ceramic reference object for use in the automatic setting-up method of the present invention.

BRIEF SUMMARY OF THE INVENTION

Machine vision equipment for determining at least one physical property of a smoking article, according to a typical embodiment, includes a camera defining a field of view and being adapted to form an image of the article within the field of view, and a processing unit which processes the image to determine at least one physical property of the article, a first support which supports the article within the field of view at a predetermined distance from the camera, a second support which supports a reference object having at least one accurately known dimension, a moving mechanism which selectively moves at least one of the camera, the first support, and the second support such that a reference object placed on the second support is disposed within the camera's field of view at the predetermined distance from the camera, an adjusting unit which automatically adjusts the configuration of the camera, a processor which determines the optimum configuration of the camera by processing at least one image of a reference object placed on the second support, and a controller which controls operation of the moving mechanism, camera, adjusting unit, and processor in order to bring a reference object supported by the second support into the camera's field of view, to image the reference object, to determine the optimum configuration of the camera, and to adjust the camera to the optimum configuration.

Following is a description by way of example only with reference to the accompanying drawings of embodiments of the present invention:

BRIEF DESCRIPTION OF THE SEVERAL VIEWS OF THE DRAWINGS

FIG. 3 is graph which shows an illustrative, non-linear relationship between pixels and actual distance for a digital camera.

DETAILED DESCRIPTION OF THE INVENTION

Figure 1:
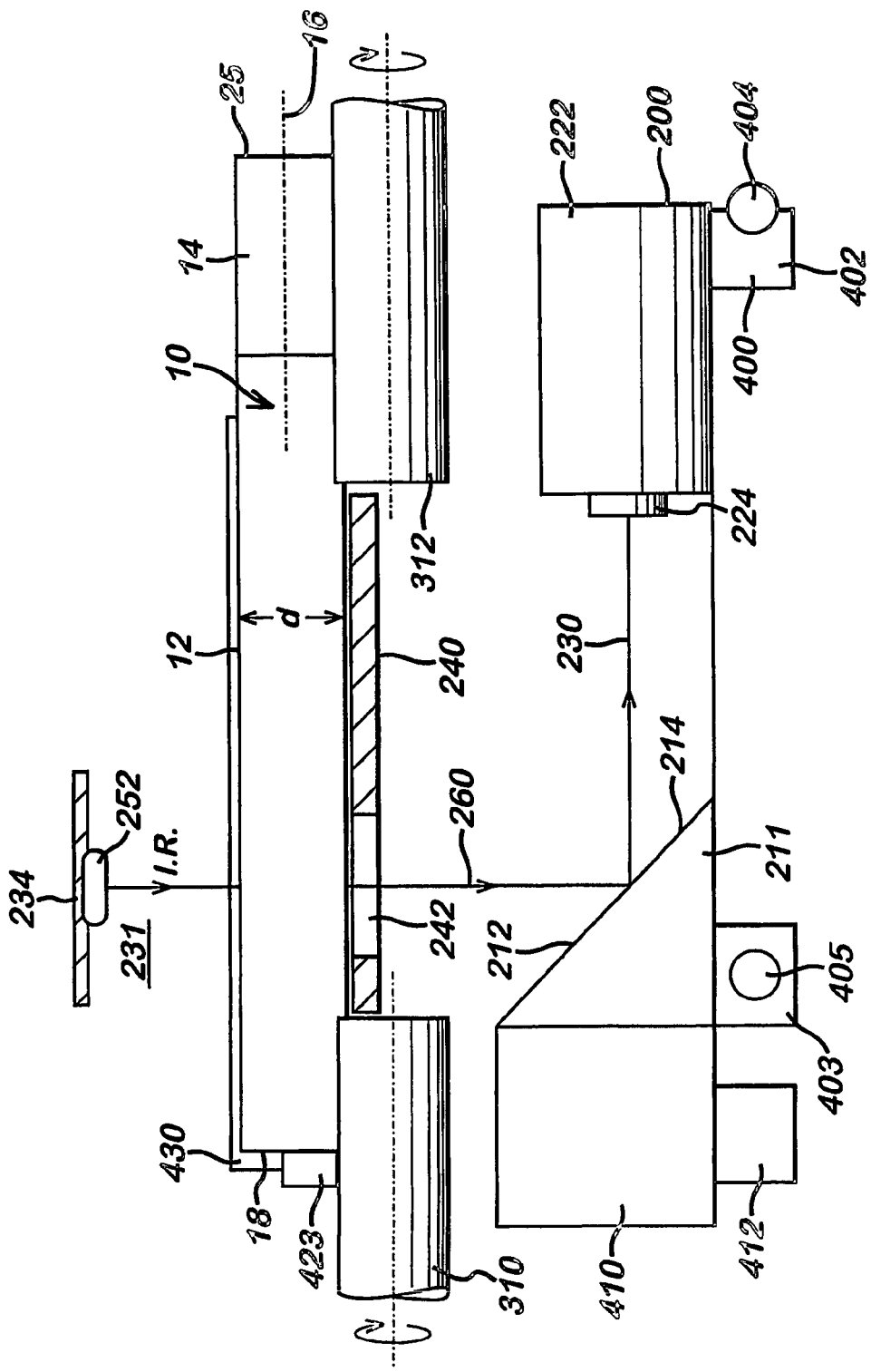
FIG. 1 is a schematic side view of machine vision equipment in accordance with the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Co-pending international patent application no. PCT/GB2004/001181 discloses machine vision equipment for measuring one or more physical properties of a rolled smoking article or filter rod such, for example, as a cigarette 10. As described above, the present invention relates to improvements in or relating to such machine vision equipment, and accordingly, full details of the construction and operation of the machine vision equipment are not repeated herein; the following describes the machine vision equipment only to the extent that is necessary to describe the improvements provided by the present invention.

Thus, as described in PCT/GB2004/001181, machine vision equipment comprises a vision system 200 comprising a digital near infra-red video camera 222 and having a barrel portion 224 accommodating a lens (not shown) which defines a first optical axis 230. The vision system 200 is connected to a suitable computer control system (not shown) which includes a frame-grabber device adapted to receive and capture and video signal from the camera 222. The barrel portion 224 is formed with a gear (not shown) which is drivable by a DC motor for automatically adjusting the focal length of the camera 222.

In accordance with the present invention, said camera 222 is mounted on a carriage 400 which comprises two substantially parallel, depending slides 402, 403 which are adapted to engage respective spaced parallel rods 404, 405, to allow horizontal translational movement of the carriage 400 in a direction substantially orthogonally to said first optical axis 230.

Spaced from the camera 222, the carriage 400 carries an upstanding piece 211 of generally triangular cross-section having an inclined face 212. Said inclined face 212 is aligned with the first optical axis 230, and subtends an angle of about 45° thereto in a 25 vertical plane, and is oriented substantially orthogonally to the first optical axis 230 in a horizontal plane; said inclined face 212 carries a planar mirror 214 for reflecting light on said first optical axis 230 through 90° to a second substantially vertical optical axis 260.

Figure 2:
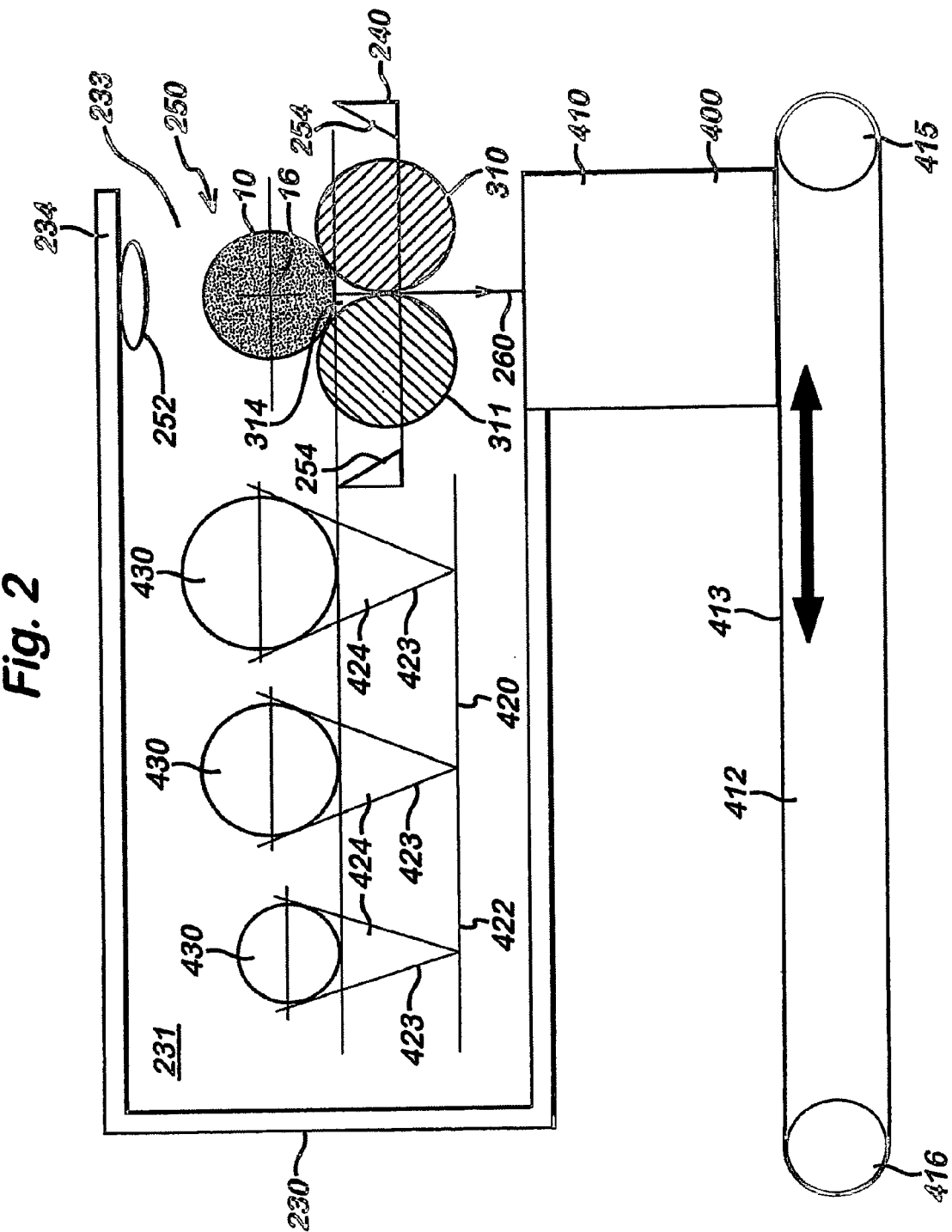
FIG. 2 is a schematic end view of machine vision equipment in accordance with the present invention.

Juxtaposed said upstanding piece 211, the carriage 400 includes a mounting block 410 which is fixedly secured, as best shown in FIG. 2, to a belt drive 412 for driving the carriage 400 translationally along said rods 404, 405.

The belt drive 412 comprises an endless belt 413 which extends around two spaced rollers for 415, 416. Said belt drive 412 is connected to a selectively operable servo-motor (not shown) under the control of said computer control system.

With reference to FIG. 2, said carriage 400 further comprises a bracket 230 in the form of an elongated C having a substantially horizontal upper portion 234 and defining a recess 231 which is open at one end 233 substantially in line with said second optical axis 260. On its underside, the upper portion 234 carries an infra-red back-light 252 which is selectively operable to produce a 3 mm wide collimated beam. Said back-light 252 is substantially aligned at the second optical axis 260.

Within said recess 231, at said open end 233, the bracket 230 supports a substantially horizontal, generally planar jig member 240 having an aperture 242 formed therein in alignment with the second optical axis 260. Being fixedly secured to the bracket 230, the jig member 240 is moveable with the carriage 400, and carries two laterally spaced diffuse infra-red side-lights 254 which are positioned respectively on opposite sides of the aperture 242, obliquely of the second optical axis 260. The infra-red back-light 252 and infra-red side-lights 254 are connected to a power control box (not shown) which is adapted to receive control signals from said frame-grabber. Said side-lights 254 can be actuated independently of said back-light 252, and serve to illuminate an object space 250 defined by the upper portion 234 of the brackets 230 and the jig member 240 with diffuse infra-red light.

Circumjacent to the back-light 252, the underside of said upper portion 234 forms a background for the object space 250 and is uniformly dark to give good contrast with an object to be imaged within said object space 250.

Fixedly secured above the carriage 400 are two opposing pairs of rollers 310, 311; 312 forming part of a transport system for a rolled smoking article or filter rod 10 to be imaged using the vision system 200. Each pair of rollers 310, 311; 312 comprises two juxtaposed rollers which define a respective upper, generally V-shaped groove 314 at substantially the same level as the jig member 240. The rollers 310, 311; 312 are oriented substantially parallely to the first optical axis 230, substantially orthogonally to the direction of movement of the carriage 400, and are positioned on opposite sides of the jig member 240, with their respective V-shaped grooves 314 in alignment.

The rollers 310, 311; 312 are configured to support slidingly a rolled smoking article or filter rod, such as cigarette 10 as shown in FIGS. 1 and 2. The transport system comprises a pusher (not shown) for pushing the cigarette 10 axially along the V-shaped grooves 314 defined by the respective pairs of rollers 310, 311; 312, and the rollers and jig member 240 are positioned so that the cigarette can be transferred smoothly from one pair of rollers 310, 311 to the other pair 312 via the jig member 240. The rollers 310-312 are connected to the computer control system and are adapted to rotate about their respective axes as shown in FIG. 1 so as to rotate the cigarette 10 about its longitudinal axis 16 for reasons described in co-pending PCT/GB2004/001181.

The rollers 310-312 are further configured and arranged so as to define a clearance between each pair of rollers 310, 311; 312 and the respective side of the jig member 240, so that upon operation of the belt drive 412, the jig member 240 can be withdrawn from the space between the two opposing pairs of rollers 310, 311; 312 without interference and, upon reversal of the belt drive 412, re-inserted into that space.

Mounted within said recess 231 is a fixed plate 420 which is generally U-shaped in plan view. Said U-shaped plate 420 comprises two arms, one of which 422 is shown in FIG. 2. Each arm 420 carries on its upper surface a plurality of generally V-shaped holder members 423. Each holder member 423 on one arm 422 is aligned with a corresponding holder member 423 on the other arm of the U-shaped plate 420. In the embodiment shown in FIG. 2, each arm 422 supports three holder members 423.

The U-shaped plate 420 is positioned such that when the belt drive 412 is operated to move the carriage 400, the second optical axis 260 of the camera 222 traverses the space between the two arms 422 of the new-shaped plate 420.

The pairs of holders members 423 are adapted for releasably supporting respective reference objects 430 of different respective sizes.

Each reference object 430 is fabricated from a highly dimensionally stable alumina ceramic material, and has a precisely machined cylindrical shape having an accurately known respective diameter. In FIG. 2, the three reference objects 430 are of three different sizes, namely relatively small, relatively large and intermediate. For the sake of illustration, the differences in size between the reference object 430 have been greatly exaggerated in FIG. 2. In practice, the diameters of the reference object 430 are selected to provide three calibration points for calibrating the vision system 200 as described in more detail below. The diameters are chosen to provide calibration points at the upper and lower extremities and substantially in the middle of the expected range of measured diameters of the cigarette 10. Five different reference objects 430 may be provided having the following diameters:

4.9 mm+/−0.0025 mm
5.75 mm+/−0.00025 mm
6.6 mm+/−0.00025 mm
7.45 mm+/−0.00025 mm
8.3 mm +/−0.00025 mm

By selecting any three successive objects 430 from the above, the five objects can be used to provide three-point calibration across three different measurement ranges as described below.

A preferred material for making the cylindrical reference objects 430 is "Alsint 99, 7" which is commercially available from W Haldenwanger Technishe Keramik GmbH & Co KG, Germany, and comprises about 99.7% wt. alumina, with the remainder being mainly magnesium oxide.

As best shown in FIG. 2, a cigarette 10 supported by the juxtaposed rollers 310-312 will sit in the respective grooves 314 at a predetermined height above the mirror 214 and thus at a predetermined optical distance from the camera 222. The distance of the central axis 16 of the cigarette 10 from the camera 222 will vary depending on the diameter of the cigarette 10. In order to calibrate the vision system 200 accurately, it is desirable that the reference objects 430 should be positioned accurately at the same distance from the camera 222. Accordingly, the V-shaped holders 423 are shaped to replicate the shape of the grooves 314 in the respective pairs of rollers 310, 311; 312, such that a reference object 430 of any of the aforementioned diameters will sit in the V-shaped recess 424 defined by the holders 423 at the same height above the mirror 214.

The operation of the machine vision equipment in accordance with the present invention is now described.

The vision system 200 of the equipment is adapted to form a digital image of the profile of a rolled smoking article or filter rod, such as a cigarette 10, supported by the rollers 310-312 and jig member 240. As the cigarette 10 is pushed slidingly along the grooves 314, the part of the cigarette 10 that is imaged is the part that is visible through the aperture 342 formed in the jig member 240. The video output from the camera 222 is sampled by the frame-grabber and processed by the computer control system in accordance with standard vision block techniques. The side lights 254 are actuated as required to light the cigarette 10 with diffuse light against the uniformly dark background formed on the underside of the upper portion 234 of the bracket 230. The shutter speed of the camera 222 is adjusted to provide good contrast between the cigarette 10 and the dark background, without undue exposure which might give rise to unwanted "blooming" phenomena. Preferably, the video camera is operated in field mode, with its major axis oriented substantially orthogonally to the minor axis of the cigarette 10 to take advantage of the full resolution of the camera.

In order to measure the diameter (d) of the cigarette 10, for example, an image of the profile of the cigarette 10 is processed by the computer control system to detect in the image the two parallel, opposite edges of the profile. As described above, suitable imaging software may be run on the computer control system for analysing the image using well known algorithms for detecting edges. Such algorithms typically comprehend measuring contrast levels for defining a point at which an edge is defined as being present, the length in pixels along the defined edge being used to determine a contiguous and true edge, and involve statistical considerations to determine the probability that a detected edge is a true edge. An edge may be detected by analysing horizontal and vertical region projections of the image as described, for example, by Sonka, et al., 1999 *Image Processing, Analysis and Machine Vision, 2nd Edition*, page 256 (6.35), Pacific Grove: PWS Publishing, ISBN 0-534-95393-X, the contents of which are incorporated herein by reference.

In order to provide an accurate measurement of distance such, for example, as diameter (d) it is necessary for the camera 222 to be properly focused on the test object in the object space 250, and for the vision system 200 to be properly calibrated to convert pixel distances into actual distances.

Thus in order to set-up the machine vision equipment in accordance with the present invention, the computer control system actuates the belt drive 412 to move the carriage 400 translationally such that the second optical axis 260 is positioned directly in alignment with one of the reference objects 430 supported by the V-shaped holder members 423. Part of the selected reference object 430 is visible to the camera 222 through the space between the two arms 422 of the U-shaped plate 420 and the aperture 242. For auto-focusing the camera 222, it is preferred to use the middle reference object 430. Under control of the computer control system the focal length of the camera 222 is then adjusted progressively using the DC motor to drive the gear formed in the barrel portion 224 of the camera 222, and the image of the reference object 430 is serially sampled to form a series of image samples. The image samples are then analysed by the computer control system using the image analysis algorithms of the kind referred to above to determine the image sample, and thus position of the barrel portion 224 of the camera 222, in which the edges of the profile of the reference object 430 in the image are best in focus. Having established the correct focal length of the camera 222 the DC motor is operated again to return the barrel portion 224 to the correct in-focus position.

All three reference objects 430 are then used to calibrate the vision system 200, by imaging each of the three reference objects 430 in turn. Thus, the belt drive 412 is operated to move the carriage 400 such that one of the end-most reference objects 430 is visible to the camera 222. With the camera 222 focused as mentioned above, the image of the profile of the reference object 430 which is visible through the U-shaped plate 420 and aperture 242 is sampled by the frame-grabber, and the image sample is processed to detect the two straight, opposite edges of the profile. The distance between the two straight edges is equal to the diameter of the reference object 430.

It will be appreciated that the profile of each reference object corresponds to a cross-section of the reference object 430 through its central axis 16. The vision system 200 is also focused, as described above, on the central axis 16 of the middle reference object 430, and for the reasons described above, the central axes 16 of the other two referenced objects are disposed at slightly different optical distances from the camera 222 from the distance of the central axis of the middle reference object 430. However, these differences in distance are within the tolerance of the focus of the camera 222, and it is not necessary to re-focus the camera 222 on each different reference object 430.

Having measured the diameter of the one end-most reference object 430, the belt drive 412 is then operated to bring the camera 222 into alignment with the middle reference object 430, and its diameter is measured. Finally, the diameter of the other end-most reference object 430 is determined as described above.

Since the respective diameters of the three reference objects 430 are accurately known, the measured diameters can be used to generate a three-point calibration curve as shown in FIG. 3 which is non-linear owing to well-known visual effects associated with digital cameras. As described above, combinations of three sequential reference objects 430 selected from five different reference objects can be used to provide three point calibrations across three different measurement ranges. In FIG. 3, these three ranges are represented by the symbols ○, ◯ and +.

The calibration curve generated by the computer control system is stored in the computer's memory, and the belt drive 412 is then returned to its start position such that the jig member 240 is disposed in the space interposing the opposing ends of the pairs of rollers 310, 311; 312 as described above. The machine vision equipment in accordance with the present invention is then set-up to measure one or more physical properties, particularly the dimensions, including diameters, of test objects in the object space 250 carried by the rollers 310, 311; 312 in accordance with co-pending PCT/GB2004/001181.

In case the focus or calibration of the vision system 200 should drift during use, the control system may be programmed to interrupt testing of test objects intermittently and to re-focus and re-calibrate the vision system 200 as described above.

The present invention thus provides improvements in or relating to machine vision equipment of the kind described in co-pending PCT/GB2004/001181 by providing automated setting-up of the cameras 222 focus and calibration of the vision system using a plurality of reference objects in the form of accurately fabricated ceramic cylindrical bars.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. Machine vision equipment for determining at least one physical property of a smoking article, the equipment comprising:

a camera defining a field of view and being adapted to form an image of said article within said field of view, and a processing unit which processes said image to determine at least one physical property of said article;

a first support which supports said article within said field of view at a predetermined distance from said camera;

a second support which supports a reference object having at least one accurately known dimension;

a moving mechanism which selectively moves at least one of the camera, the first support, and the second support such that a reference object placed on the second support is disposed within the camera's field of view at said predetermined distance from said camera;

an adjusting unit which automatically adjusts the configuration of the camera;

a processor which determines the optimum configuration of said camera by processing at least one image of a reference object placed on the second support; and a controller which controls operation of said moving mechanism, camera, adjusting unit, and processor in order to bring a reference object supported by said second support into the camera's field of view, to image said reference object, to determine the optimum configuration of the camera, and to adjust the camera to said optimum configuration, wherein said camera comprises a digital camera which is adapted to form said image as a regular array of pixels.

2. Machine vision equipment as claimed in claim 1, wherein said processor is adapted to determine the optimum configuration of the camera by processing a plurality of images of said reference object obtained with said camera in different respective configurations, and said controller is adapted to control said camera, adjusting unit, and processor to obtain and process serial images of said reference object whilst adjusting progressively the configuration of the camera, and to determine the optimum configuration on the basis of said serial images.

3. Machine vision equipment as claimed in claim 2, wherein said adjusting unit is adapted to adjust the focal length of the camera, said processor is arranged to determine optimum focal length, and said controller is adapted to control the adjusting unit, camera, and processor to obtain and process serial images of the reference object at different respective focal lengths, and to determine the optimum focal length at which the reference object is best in focus, and to control the adjusting unit thereafter to adjust the focal length of the camera to said optimum focal length.

4. Machine vision equipment as claimed in claim 1, wherein said second support is configured to support a reference object having substantially the same shape and size in substantially the same orientation in said field of view as said article.

5. Machine vision equipment as claimed in claim 1, wherein said processor is adapted to compare an actual measured value of said at least one dimension of said reference object with said accurately known value, said adjusting unit is adapted to adjust the calibration of said imaging unit, and said controller is configured to control said camera, processor and adjusting unit to measure said at least one dimension of said reference object to obtain a measured value, to compare said measured value with the accurately known value, and to adjust the calibration of the camera accordingly such that the measured value equals the known value.

6. Machine vision equipment as claimed in claim 5, wherein said second support is adapted to support a plurality of reference objects, each having substantially the same shape as said article, but each having a different respective, accurately known value of said at least one dimension; said moving mechanism is adapted to move selectively one or more of the camera, the first support and the second support to bring each reference object in turn into the camera's field of view at the said predetermined distance from the camera; and said processor is adapted to compare the measured value of said at least one dimension of each reference object with the respective accurately known value, and to generate a calibration curve for said camera on the basis of said comparisons.

7. Machine vision equipment as claimed in claim 6, wherein said second support is adapted to support three or more reference objects.

8. Machine vision equipment as claimed in claim 7, wherein each reference object comprises a cylindrical bar of accurately known diameter.

9. Machine vision equipment as claimed in claim 8, wherein said second support comprises at least one holder for holding each reference object, each holder defining a V-shaped cavity which is configured to receive transversely a cylindrical reference bar at the same depth into the cavity regardless of the diameter of the bar.

10. Machine vision equipment as claimed in claim 9, wherein said second support comprises two holders for holding each reference object, one holder at or towards each end of the respective bar.

11. A method of setting-up machine vision equipment, which equipment is arranged to determine at least one physical property of a smoking article, the equipment comprising a camera defining a field of view and being adapted to form an image of said article within said field of view, and a processor which processes said image to determine at least one physical property of said article, and a first support which supports said article at a predetermined distance from said camera within said field of view; said method comprising the steps of:

providing a second support to support at least one reference object;

placing a reference object having at least one accurately known dimension on said second support;

selectively moving at least one of said camera, said first support and said second support, such that said reference object is brought into the camera's field of view at said predetermined distance from said camera;

imaging said reference object to obtain at least one image, and processing said at least one image to determine the optimum configuration of the camera and thereafter adjusting the configuration of said camera to said optimum configuration; and obtaining an image of said reference object and measuring said at least one dimension, comparing the measured value of said dimension with the accurately known value, and thereafter adjusting the calibration of the camera such that the measured value substantially equals the known value.

12. A method as claimed in claim 11, comprising obtaining and processing a series of images of said reference object whilst adjusting progressively the configuration of the camera, and determining the optimum configuration on the basis of said series of images.

13. A method as claimed in claim 12, comprising adjusting the focal length of the camera while obtaining and processing serial images of the reference object to determine the optimum focal length at which the reference object is best in focus; and thereafter adjusting the focal length of the camera to said optimum focal length.

14. A method as claimed in claim 13, comprising placing on said second support a reference object having substantially the same shape and size in substantially the same orientation in said field of view as the test object.

15. A method as claimed in claim 11, wherein said camera comprises a digital camera which is adapted to form said image as a regular array of pixels.

16. A method as claimed in claim 11, comprising supporting a plurality of reference objects on said second support, each reference object having substantially the same shape as said article, but each having a different respective, accurately known value of said at least one dimension, selectively moving at least one of the camera, the first support and the second support to bring each reference object in turn into the camera's field of view at the said predetermined distance from the camera, comparing the measured value of said at least one dimension of each reference object with the respective accurately known value, and generating a calibration curve for said camera on the basis of said comparisons.

17. A method as claimed in claim 16, comprising supporting three reference objects on the second support, and imaging those reference objects to produce a calibration curve based on three points.

18. A method as claimed in claim 17, wherein each reference object comprises a cylindrical bar of accurately known diameter.

19. A method as claimed in claim 18 comprising supporting each reference object on least one respective holder, said holder defining a V-shaped cavity which is configured to receive a transverse cylindrical reference bar at the same depth into the cavity regardless of the diameter of the bar.

20. A method as claimed in 19, wherein said second support comprises two holders for holding each reference object, one holder at or towards each end of the respective bar.

21. A method of setting-up machine vision equipment, which equipment is arranged to determine at least one physical property of a smoking article, the equipment comprising a camera defining a field of view and being adapted to form an image of said article within said field of view, and a processor which processes said image to determine at least one physical property of said article, and a first support which supports said article at a predetermined distance from said camera within said field of view; said method comprising the steps of:

providing a second support to support at least one reference object;

placing a reference object having at least one accurately known dimension on said second support;

selectively moving at least one of said camera, said first support and said second support, such that said reference object is brought into the camera's field of view at said predetermined distance from said camera; and imaging said reference object to obtain at least one image, and processing said at least one image to determine the optimum configuration of the camera and thereafter adjusting the configuration of said camera to said optimum configuration, wherein said camera comprises a digital camera which is adapted to form said image as a regular array of pixels.

22. A method as claimed in claim 21, comprising obtaining and processing a series of images of said reference object whilst adjusting progressively the configuration of the camera, and determining the optimum configuration on the basis of said series of images.

23. A method as claimed in claim 22, comprising adjusting the focal length of the camera while obtaining and processing serial images of the reference object to determine the optimum focal length at which the reference object is best in focus; and thereafter adjusting the focal length of the camera to said optimum focal length.

24. A method as claimed in claim 23, comprising placing on said second support a reference object having substantially the same shape and size in substantially the same orientation in said field of view as the test object.

* * * * *